(12) United States Patent
Ingle et al.

(10) Patent No.: US 9,888,953 B2
(45) Date of Patent: *Feb. 13, 2018

(54) NESTED BALLOON CRYOTHERAPY

(71) Applicant: BOSTON SCIENTIFIC SCIMED, INC., Maple Grove, MN (US)

(72) Inventors: Frank Ingle, Palo Alto, CA (US); Rebecca Tin, Sunnyvale, CA (US); Robert F. Bencini, Sunnyvale, CA (US); James Mazzone, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 300 days.

This patent is subject to a terminal disclaimer.

(21) Appl. No.: 14/712,405

(22) Filed: May 14, 2015

(65) Prior Publication Data
US 2015/0250525 A1 Sep. 10, 2015

Related U.S. Application Data

(63) Continuation of application No. 13/019,138, filed on Feb. 1, 2011, now Pat. No. 9,033,965.

(60) Provisional application No. 61/300,220, filed on Feb. 1, 2010.

(51) Int. Cl.
*A61B 18/02* (2006.01)
*A61B 18/00* (2006.01)

(52) U.S. Cl.
CPC .... *A61B 18/02* (2013.01); *A61B 2018/00255* (2013.01); *A61B 2018/0212* (2013.01)

(58) Field of Classification Search
CPC .......... A61B 18/02; A61B 2018/00255; A61B 2018/0212
USPC ...................................... 606/21–26
See application file for complete search history.

(56) References Cited

U.S. PATENT DOCUMENTS

| | | | |
|---|---|---|---|
| 7,740,627 B2 | 6/2010 | Gammie et al. | |
| 8,187,261 B2 | 5/2012 | Watson | |
| 8,439,906 B2 | 5/2013 | Watson | |
| 8,465,481 B2 | 6/2013 | Mazzone et al. | |
| 8,715,274 B2 | 5/2014 | Watson | |
| 2002/0007180 A1 | 1/2002 | Wittenberger et al. | |
| 2002/0045893 A1* | 4/2002 | Lane | A61B 18/02 606/21 |
| 2002/0045894 A1 | 4/2002 | Joye et al. | |
| 2003/0060762 A1* | 3/2003 | Zvuloni | A61B 18/02 604/113 |
| 2003/0187428 A1 | 10/2003 | Lane et al. | |
| 2010/0100087 A1 | 4/2010 | Mazzone et al. | |

(Continued)

*Primary Examiner* — Michael Peffley
*Assistant Examiner* — Khadijeh Vahdat
(74) *Attorney, Agent, or Firm* — Faegre Baker Daniels LLP

(57) ABSTRACT

A cryotherapy system includes a cryotherapy catheter having an inflatable balloon portion and a pressure regulator. The inflatable balloon portion includes an outer balloon and an inner balloon within the outer balloon. The inner balloon is configured to receive during a cryotherapy procedure a cryogenic agent for extracting heat from body tissue at a desired location. The inflatable balloon portion is at a distal end of the cryotherapy catheter. The pressure regulator is adapted to maintain a positive pressure between the inner balloon and the outer balloon during a cryotherapy procedure.

20 Claims, 8 Drawing Sheets

(56) References Cited

U.S. PATENT DOCUMENTS

2012/0158104 A1   6/2012   Huynh et al.

* cited by examiner

NESTED BALLOON CRYOTHERAPY

CROSS-REFERENCE TO RELATED APPLICATIONS

This application is a continuation of U.S. application Ser. No. 13/019,138, filed on Feb. 1, 2011, now U.S. Pat. No. 9,033,965, which claims priority from the earlier filed U.S. Provisional Application No. 61/300,220, filed Feb. 1, 2010, the entire disclosures of which are incorporated herein by reference.

BACKGROUND

Atrial fibrillation is a condition that results from abnormal electrical activity within the heart. This abnormal electrical activity may originate from various focal centers of the heart, and the electrical activity generally decreases the efficiency with which the heart pumps blood. It is believed that some of the focal centers reside in the pulmonary veins of the left atrium. It is further believed that atrial fibrillation can be reduced or controlled by structurally altering or ablating the tissue at or near the focal centers of the abnormal electrical activity to form a "conduction block."

One method of structurally altering tissue of the heart and pulmonary veins is to make, for example during open-heart surgery, a series of incisions in a maze-like pattern in the atria, and sew the incisions back together. As the incisions heal, scar tissue forms, and the scar tissue may block the conductive pathways thought to cause atrial fibrillation. The procedure, which was developed under the direction of Dr. James Cox and refined over a period of years, may be referred to as a "maze" procedure, a "Cox maze" procedure, a "Cox maze III" procedure; or the procedure may be referred to by various other names.

A less invasive method of structurally altering heart tissue and pulmonary veins involves ablating tissue through the use of an ablation catheter. One type of ablation catheter, for example, delivers radio frequency (RF) energy to ablate tissue; another example ablation catheter ablates tissue with a heat source; another example ablation catheter delivers cryotherapy to ablate tissue by freezing it.

Cryotherapy may be delivered to an appropriate treatment site inside a patient's heart or circulatory system with a cryotherapy catheter. A cryotherapy catheter generally includes a treatment member at its distal end, such as an inflatable balloon having a cooling chamber inside. To deliver the cryotherapy, the inflatable balloon may be introduced at a treatment site inside a patient, and the balloon may be positioned and inflated. Once the balloon is positioned, a cryogenic agent may be provided by a source external to the patient at the proximal end of the cryotherapy catheter, and delivered distally through a lumen to the cooling chamber, where it may be released. Release of the cryogenic agent into the chamber can cool the chamber (e.g., through the Joule-Thomson effect), and correspondingly, the balloon's outer surface, which may be in contact with tissue that is to be ablated. Gas resulting from release of the cryogenic agent may be exhausted proximally through an exhaust lumen to a reservoir or pump external to the patient. As a result of the release of the cryogenic agent into the chamber and the exhausting of the resulting gas from the chamber, tissue adjacent to the balloon may be cooled to a therapeutic level (e.g., 0° C., −20° C., −40, −60° C., −80° C., or some other appropriate value) for an appropriate period of time.

SUMMARY

When a cryotherapy catheter is employed to deliver cryotherapy to a treatment site internal to a patient, such as to a patient's left or right atrium (e.g., to treat atrial fibrillation), it may be advantageous to focus the cryotherapy on a precise region of tissue to be treated. In order to focus the cryotherapy on a precise location, portions of the outer surface of an inflatable balloon portion can be insulated from the cryogenic agent by having nested balloons. For example, an inner balloon can be adapted to receive the cryogenic agent and an outer balloon can be spaced from the inner balloon such that its external surface is thermally insulated from a cryogenic agent internal to the inner balloon. The cryotherapy can then be delivered by manipulating the cryotherapy catheter such that the inner balloon contacts a portion of the outer balloon adjacent to a desired target tissue region. The remainder of the outer balloon can remain spaced from the inner balloon to insulate and protect non-targeted tissue that may be in contact with the outer surface of the outer balloon during a treatment procedure. The thermally insulated regions can also protect other bodily fluids that may come into contact with the outer balloon (e.g., blood). An insulating space can be maintained between the inner balloon and the outer balloon by applying a positive pressure between the two balloons.

A pressure regulator can be used to maintain the positive pressure between the two balloons. In some embodiments, the pressure regulator is a valve that can be closed to maintain a desired amount of fluid within the space between the outer balloon and the inner balloon. In other embodiments, the pressure regulator can include one or more fluid flow controllers to control the flows of fluid into and/or out of the space between the outer balloon and the inner balloon. Leaks in one or both of the balloons can be detected by monitoring the pressure within the space between the two balloons with a pressure sensor. In some embodiments, the outer balloon can include a wall having compressible structures that can be compressed to reduce the insulative effect of the outer wall.

In a first aspect, a cryotherapy system includes a cryotherapy catheter having an inflatable balloon portion and a pressure regulator. The inflatable balloon portion includes an outer balloon and an inner balloon within the outer balloon. The inner balloon is configured to receive, during a cryotherapy procedure, a cryogenic agent for extracting heat from body tissue at a desired location. The inflatable balloon portion is at a distal end of the cryotherapy catheter. The pressure regulator is adapted to maintain a positive pressure between the inner balloon and the outer balloon during a cryotherapy procedure.

The cryotherapy system can include a detector to monitor the pressure between the inner balloon and the outer balloon and to determine whether a leak of the inner or outer balloon has occurred. For example, a leak of the outer balloon can be detected by a decrease of the pressure between the inner balloon and the outer balloon; and a leak of the inner balloon can be detected by an increase of the pressure between the inner balloon and the outer balloon.

The pressure regulator can maintain a positive pressure between the inner balloon and the outer balloon sufficient to maintain a gas space between the inner balloon and the outer balloon when the outer balloon is within a body lumen. For example, the pressure regulator can maintain a positive pressure of between 0.1 and 2 psi greater than blood pressure. In some embodiments, the pressure regulator is a valve and the positive pressure is maintained by closing the valve once a space between the outer balloon and the inner balloon is filled with a predetermined amount of fluid.

The outer balloon can be more compliant than the inner balloon. The outer balloon can be made of a polymer. In some embodiments, the outer balloon is a thermoplastic elastomer, such as polyether block amide, which is sold under the trade name Pebax®. In other embodiments, the outer balloon can be a urethane. The inner balloon can be made of polyolefin copolymer, polyester, polyethylene tera-phthalate, polyethylene, polyether-block-amide, polyamide, polyimide, latex, a urethane-family material, neoprene, and poly ether amide block copolymer.

The outer balloon, in some embodiments, includes a wall having compressible structures that can be compressed to reduce the insulating properties of the wall of the outer balloon. The compressible structures can be selected from the group consisting of air pockets, liquid pockets, gel pockets, dimples, open cell foam, and combinations thereof.

In another aspect, a cryotherapy catheter includes an inflatable balloon portion at a distal end of the cryotherapy catheter. The inflatable balloon portion includes an outer balloon and an inner balloon within the outer balloon. The inner balloon is adapted to receive a cyrotherapy agent. The outer balloon has a wall including a plurality of compressible structures that provide an insulating property, such that the outer balloon can be compressed between the inner balloon and a target tissue region to reduce the insulating property of a compressed portion of the wall of the outer balloon, to extract heat from the target tissue region. In some embodiments, the plurality of compressible structures are air pockets, dimples, open cell foam, and combinations thereof.

In another aspect, a method of detecting a leak in a two-balloon cryotherapy catheter includes using a cyrotherapy catheter having a distal end that includes an inflatable balloon portion having an outer balloon and an inner balloon within the outer balloon. The method includes, introducing a distal end of the cyrotherapy catheter to a desired anatomical location, applying a positive pressure to inflate a space between the outer balloon and the inner balloon with a fluid, detecting changes in pressure of the space between the outer balloon and the inner balloon, and providing an alert adapted to notify a user of a condition if a change in pressure indicating a breach of the inner balloon or the outer balloon has occurred.

The method can include filling the inner balloon with a cryogenic agent while maintaining a positive pressure in the space between the outer balloon and the inner balloon. The method can also include manipulating the cryotherapy catheter such that a wall of the inner balloon makes contact with a wall of the outer balloon, to extract heat from a corresponding target issue region. The positive pressure in the space between the outer balloon and the inner balloon can be maintained at between 0.1 and 2 psi greater than blood pressure.

The method can include a process of retracting the distal end of the cryotherapy catheter from the desired anatomical location. The retracting step can include the steps of, deflating the inner balloon while maintaining the positive pressure in the space between the inner balloon and the outer balloon, releasing the positive pressure from the space between the outer balloon and the inner balloon to fully deflate the inflatable balloon portion, and removing the deflated inflatable balloon portion from the desired anatomical location. Another deflation process could include releasing the positive pressure between the inner and outer balloon, then deflating inner and outer balloon simultaneously, and removing the deflated inflatable balloon portion from the desired anatomical location.

In another aspect, a method of performing cryotherapy includes using a cyrotherapy catheter having a distal end that includes an inflatable balloon portion having an outer balloon and an inner balloon within the outer balloon. The method includes the steps of introducing a distal end of a cryotherapy catheter to a desired anatomical location, applying a positive pressure to inflate the space between the outer balloon and the inner balloon, filling the inner balloon with a cryogenic agent, and manipulating the cryotherapy catheter such that a wall of the inner balloon makes contact with a wall of the outer balloon to extract heat from a corresponding target issue region.

The positive pressure in the space between the outer balloon and the inner balloon can be maintained at between 0.1 and 2 psi greater than blood pressure.

The method can include a process of retracting the distal end of the cryotherapy catheter from the desired anatomical location. The retracting step can include the steps of deflating the inner balloon while maintaining the positive pressure in the space between the inner balloon and the outer balloon, releasing the positive pressure from the space between the outer balloon and the inner balloon to fully deflate the inflatable balloon portion, and removing the deflated inflatable balloon portion from the desired anatomical location. Another deflation process could include releasing the positive pressure between the inner and outer balloon, then deflating inner and outer balloon simultaneously, and removing the deflated inflatable balloon portion from the desired anatomical location.

The method can include filling the space between the inner balloon and the outer balloon with a fluid selected from the group of nitrogen, oxygen, argon, carbon dioxide, nitrous oxide, helium, krypton, sugar solutions, saline solutions, polyols, glycols, dimethyl sulfoxide, and mixtures thereof. In some embodiments, a contrast agent can be used as the insulating fluid. The methods can include filling the inner balloon with a cryotherapy agent selected from liquid nitrogen, nitrous oxide, carbon dioxide, methane, ethane, butane, propane, chlorofluorocarbons, hydrochlorofluorocarbons, and mixtures thereof.

The details of one or more embodiments are set forth in the accompanying drawings and the description below. Other features, objects, and advantages will be apparent from the description and drawings, and from the claims.

BRIEF DESCRIPTION OF DRAWINGS

Like reference symbols in the various drawings indicate like elements.

DETAILED DESCRIPTION

When a cryotherapy catheter is employed to deliver cryotherapy to a treatment site internal to a patient, such as to a patient's left or right atrium (e.g., to treat atrial fibrillation), it may be advantageous to focus the cryotherapy on a precise region of tissue to be treated. An inflatable balloon portion at a distal end of a cryotherapy catheter is used to deliver the cryotherapy. The inflatable balloon portion includes multiple nested balloons, including at least one inner balloon adapted to receive a cryogenic agent. The inflatable balloon portion also includes an outer balloon that insulates non-targeted tissue and body fluids from the cryogenic agent(s) within the inner balloon. The cyrotherapy catheter can be manipulated such that the inner balloon contacts a portion of the outer balloon to allow better heat transfer between a portion of the surface of the outer balloon and the inner balloon to extract heat (and thus deliver cryotherapy) to a target tissue region. For example, a portion of the outer balloon can be pressed against the target tissue region such that the outer balloon deforms and makes contact with the inner balloon adjacent the target tissue region.

Figure 1:
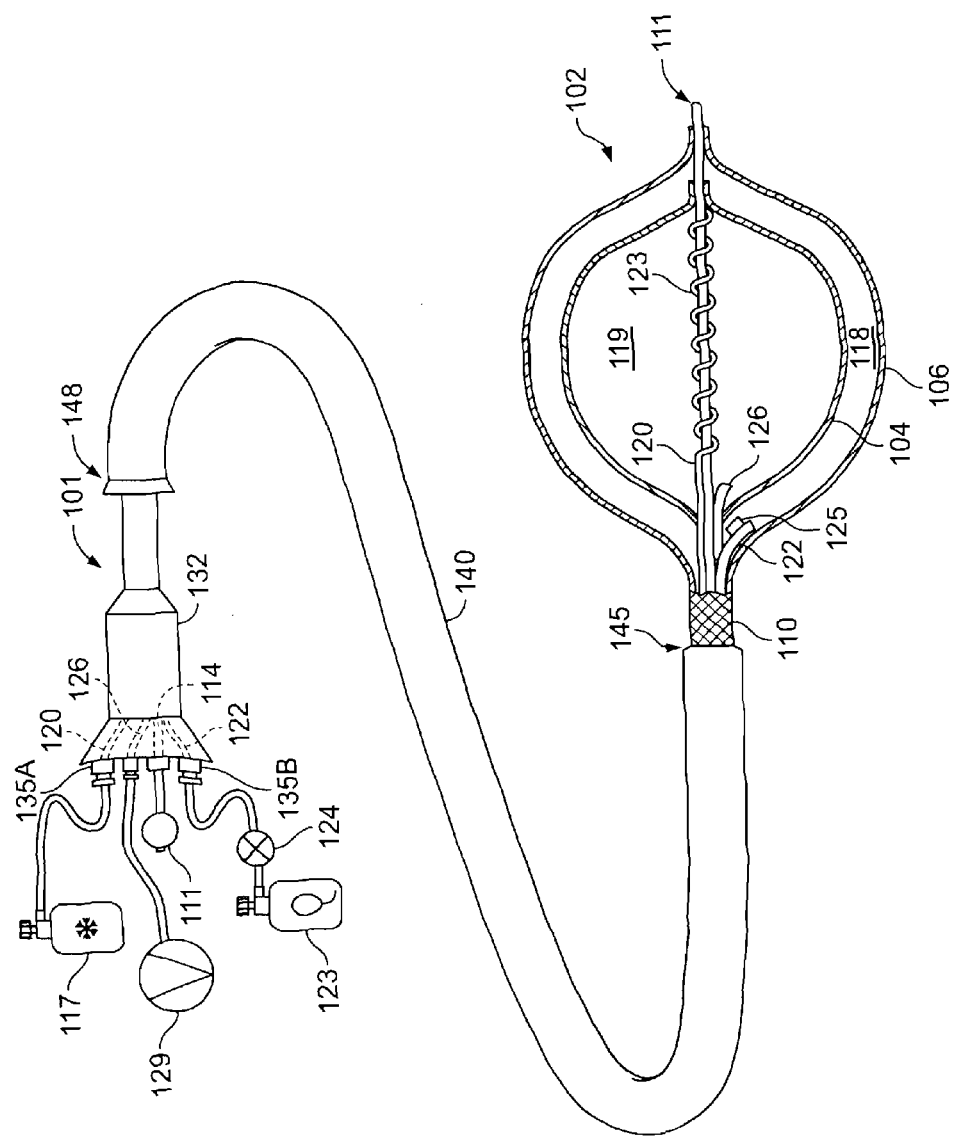
FIG. 1 illustrates an example cryotherapy catheter having two nested balloons.
Figure 2:
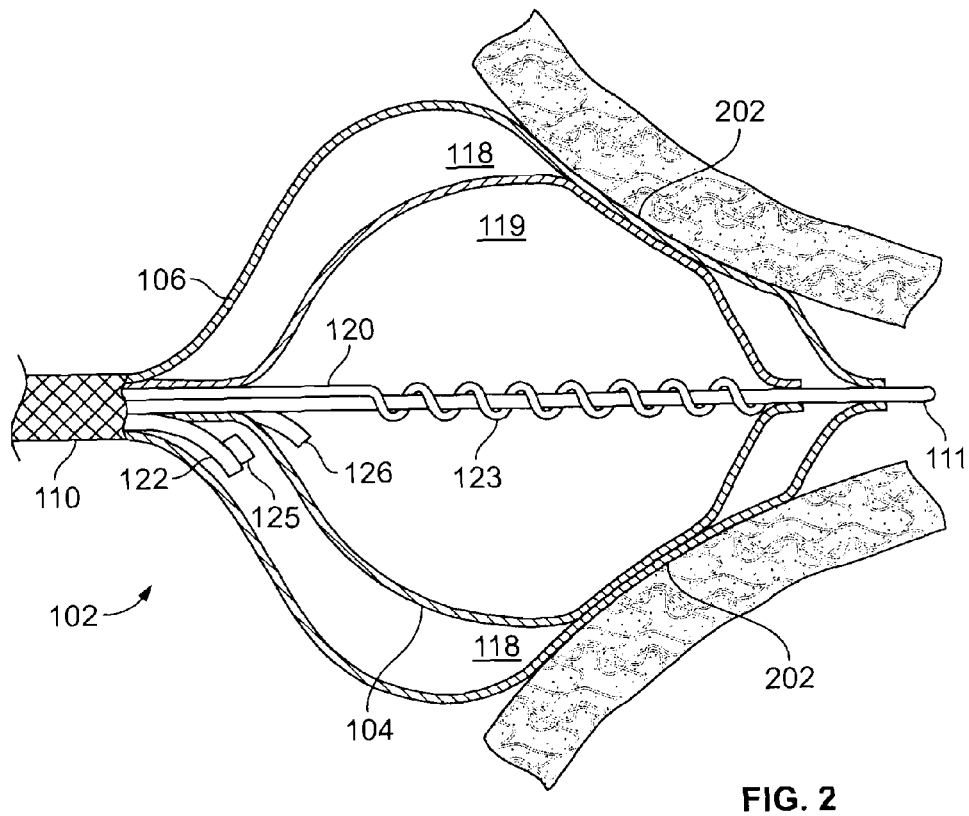
FIG. 2 illustrates an example of how the cryotherapy catheter of FIG. 1 can be used to deliver cryotherapy to a desired location.

FIG. 1 illustrates an example balloon catheter 101 having an inflatable balloon portion 102. The inflatable balloon portion 102 includes an inner balloon 104 nested within an outer balloon 106. The balloons 104 and 106 are depicted as inflated. The inner balloon 104 can be employed to deliver cryotherapy to a treatment site internal to a patient. During use, a positive pressure can be applied to and maintained in a space 118 between the inner balloon 104 and the outer balloon 106. The positive pressure can be imparted by filling the space 118 with an insulating fluid. The inner balloon 104, when inflated with a cryogenic agent, can be used to deliver cryotherapy (or more precisely, to extract heat from adjacent body tissue) by pressing the outer balloon 106 against the desired anatomical location(s) such that the inner balloon 104 makes contact with the outer balloon 106. The surrounding regions of the outer balloon 106 where the outer balloon 106 does not contact the inner balloon 104 are thermally insulated from the cooling effect of the cryogenic agent. For example, as shown in FIG. 2, when pressed against a pulmonary vein wall, the cryoablation will be limited to a contact region 202 between the two balloons. In some embodiments, the contact region can be in the form of an annular band around the outer surface of the outer balloon 106. The insulating fluid between the two balloons acts as an insulator to protect non-target tissues.

To deliver cryotherapy, the cryotherapy balloon catheter 101 shown in FIG. 1 can be configured to deliver a cryotherapy fluid (e.g., a cryogenic agent) from an external cryogenic agent source 117 to the inner balloon 104, through a cryogenic agent supply lumen 120. Inside the inner balloon 104, the cryogenic agent can be released through a cooling device 123. For example, the cooling device 123 can include a coiled portion of the supply lumen 120 having one or more orifices through which certain cryogenic agents can exit, some of which can undergo a liquid-to-gas phase change that cools the balloon 104 by evaporation. Gas resulting from the cryogenic agent being released inside chamber 119 can be exhausted through a separate exhaust lumen 126. For example, gas can be exhausted through the exhaust lumen 126 to an external vacuum pump 129. During use, the inner balloon 104 can be filled with a cryogenic agent to a pressure of between 5 psig and 15 psig. In some embodiments, the inner balloon 104 can be filled to a pressure of about 8 psig. A positive pressure can be applied to the space 118 between the inner balloon 104 and the outer balloon 106 by filling the space 118 with an insulating fluid. The insulating fluid can be introduced via an insulating fluid supply line 122 from an external insulating fluid source 123. The positive pressure can then be maintained by closing a valve 124 in the insulating fluid supply line. The space between the balloons can include a pressure sensor 125. As shown, the pressure sensor 125 is connected to an outer portion of the insulating fluid supply line. In other embodiments, the pressure sensor 125 can be positioned on an outer surface of the inner balloon 104 or on an inner surface of the outer balloon 106. In some embodiments, the pressure sensor 125 can be a pressure sensing lumen with a distal end positioned between balloons 104 and 106. The pressure sensor can be used to monitor the pressure in the space 118, which can assist the filling of the space 118, to dynamically maintain a desired positive pressure, and/or to detect the presence of leaks in either of the balloons. Leaks can be detected by monitoring the pressure of the space 118. An increase in pressure can indicate a leak in the inner balloon 104 to space 118. A drop in pressure can indicate a leak in the outer balloon 106.

The positive pressure between the outer balloon 106 and the inner balloon 104 can be maintained at a pressure of less than the pressure within the inner balloon 104 during a cryotherapy treatment but at a pressure sufficient to maintain a space between at least a portion of the inner balloon 104 and the outer balloon 106. In some embodiments, the positive pressure within space 118 can be less than 4 psig. In some embodiments, the positive pressure is greater than 0.1 psi greater than blood pressure and/or less than 2 psi greater than blood pressure. The positive pressure can be maintained at greater than 0.3 psi greater than blood pressure and less than 1.5 psi greater than blood pressure. For example, the positive pressure can be maintained at about 0.5 psi greater than blood pressure. The positive pressure maintained between the outer balloon 106 and the inner balloon 104 can impact how the outer balloon 106 conforms to anatomical structures. The lower the positive pressure, the more easily the outer balloon 106 can conform to irregular anatomical structures (e.g., an irregular PV antrum anatomy). Having the outer balloon 106 that easily conforms to anatomical structures can reduce the incidences of blood leakage past the outer balloon 106, which thus reduce the need for other measures for preventing blood leakage past the inflatable balloon portion of the cryotherapy catheter, such as applying pressure to the anatomical structures with the outer balloon or precise positioning of the outer balloon.

The elasticity of the outer balloon 106 can also impact the ability of the outer balloon 106 to conform to irregular anatomical structures. In some embodiments, the outer balloon is more complaint than the inner balloon. The outer balloon can be made of an elastic material. In some embodiments, the outer balloon 106 is more elastic than the inner balloon 104. For example, the outer balloon can be a polyether block amide, which is sold under the trade name Pebax®. In other embodiments, the outer balloon can be a urethane. The inner balloon can be formed from a polymer including, but not limited to, polyolefin copolymer, polyester, polyethylene teraphthalate, polyethylene, polyetherblock-amide, polyamide (e.g., nylon), polyimide, latex, a urethane-family material, neoprene, etc. In particular, for example, certain embodiments of the inner balloon 104 include PEBAX® 7033 material (70D poly ether amide block). In other embodiments, both the inner and outer balloon can be made of the same material, e.g., a polyether block amide. In some embodiments, the balloons 104 and/or 106 can be constructed by blow-molding a polymer extrusion into the desired shape. In other embodiments, the balloons 104 and/or 106 can be constructed by dipping a mandrel in an appropriate liquid material, and allowing the material to cure. In some embodiments, the inner balloon 104 can be constructed to expand to a desired shape when pressurized without elastically deforming substantially beyond the desired shape.

The insulating fluid can be a liquid or a gas. The particular insulating fluid can impact the function of the balloon catheter 101. For example, the specific heat capacity, the compressability, and the viscosity of the insulating fluid can all impact the function of the balloon catheter 101. The insulating fluid can be non-toxic. In some embodiments, the insulating fluid can be one or more of the following gasses: nitrogen, oxygen, carbon dioxide, argon, nitrous oxide, and helium, krypton. For example, the insulating fluid can be atmospheric air (a mixture of nitrogen, oxygen, argon, and carbon dioxide). In other embodiments, the insulating fluid can be a cryoprotectant. Cryoprotectants include sugar solutions (e.g., solutions of sucrose, trehalose, and/or glucose), saline solutions, polyols, glycols (e.g., ethylene glycol, propylene glycol, glycerol), and dimethyl sulfoxide (DMSO). The insulating fluid can include a contrast agent. For example, the insulating fluid can include iodine or barium. For example, a cryoprotectant that includes one or more radiopaque additives (e.g., iodine or barium) can be used as an insulating fluid. The use of a contrasting insulating fluid can permit a physician to track the progress of the balloons and/or to identify contact between the balloons during the delivery of cyrotherapy.

A pressure regulator can be used to maintain the positive pressure. In some embodiments, the pressure regulator can be a valve that can be closed to maintain a desired amount of fluid within the space between the outer balloon and the inner balloon. When the insulating fluid is not recirculated during a cyrotherapy procedure, a single valve can be a sufficient pressure regulator to maintain the positive pressure. In other embodiments, the insulating fluid can be recirculated during the procedure and the positive pressure can be maintained by using a pressure regulator that includes one or more fluid flow controllers that control the flow of the insulating fluid into and out of the space between the outer balloon 106 and the inner balloon 104. The pressure regulator can, in some embodiments, adjust the flow of insulating fluid based on a detected pressure within the space between the outer balloon 106 and the inner balloon 104. In some embodiments, recirculated insulating fluid can absorb ambient heat and body heat to maintain a temperature sufficient to insulate the body from the cryotherapy agent. In other embodiments, a heating system can be employed to reheat recirculated insulating fluid temperature. A temperature control system, using a temperature sensor, can be used to ensure that the insulating fluid does not fall below a predetermined temperature within the space between the outer balloon and the inner balloon.

Maintaining a positive pressure in between the inner balloon 104 and the outer balloon 106 can reduce the amount of cryogenic agent needed by reducing the amount of heat absorbed from the regions adjacent to the target anatomical location. The diameter of the cryogenic agent supply lumen 120 can be adjusted accordingly. The inner balloon 104 can be filled to a pressure of between 5 psig and 15 psig (e.g., about 8 psig). The cryogenic agent can be liquid nitrogen, nitrous oxide, carbon dioxide, methane, ethane, butane, propane, chlorofluorocarbons, hydrochlorofluorocarbons, or a mixture thereof.

Maintaining a positive pressure in between the inner balloon 104 and the outer balloon 106 during a cyrothereapy procedure (e.g., cryoablation) can also reduce complications during the retraction procedure. After a cyrothereapy procedure, the inner balloon 104 can be deflated while maintaining the positive pressure in the space between the outer balloon 106 and the inner balloon 104. The space between the balloons can then be deflated by opening valve 124. Deflating the balloons in this order can ensure that the balloons refold properly by eliminating frictional forces between the two balloons. Frictional forces can cause balloons to refold improperly. After the balloons are deflated and refolded, the distal end of the balloon catheter 101 can be removed from the body. Improperly folded balloons can complicate the retraction process (e.g., by making the retraction of balloons into a sheath 140 difficult). An improperly retracted inflatable balloon portion can cause damage to body vessels as the cryotherapy catheter is removed.

To facilitate coupling the catheter 101 to external equipment, such as the source 117 of a cryogenic agent, the source 123 of an insulating fluid, or the vacuum pump 129, the catheter 101 can include a port component 132 having a number of coupling members 135A, 135B, and 135C. The coupling members 135A, 135B, and 135C can, in some embodiments, terminate lumens that are internal to the catheter shaft (e.g., the cryogenic agent supply lumen 120, the insulating fluid supply lumen 122, and the exhaust lumen 126) with connectors (e.g., industry-standard medical connectors, proprietary medical connectors, other connectors, etc.) that facilitate connection of the lumens 120, 122, and 126 to the external equipment (e.g., with medical tubing). As shown in FIG. 1, the port component 132 is merely exemplary. Other connections and configurations are possible and contemplated (e.g., connections for pressure sensor(s), electrical sensor(s), multiple vacuum ports, etc.).

In the example of FIG. 1, the balloon catheter 101 is an over-the-wire cryotherapy balloon catheter, having a guidewire 111 disposed inside a guidewire lumen 114. In the implementation depicted, the port component 132 can also provide access to the guidewire lumen 114 and corresponding guidewire 111. In other embodiments, the balloon catheter can be free of the guidewire 111. In some embodiments, the balloon catheter 101 can have other means for maneuvering the balloon catheter 101 though the circulatory system.

As shown in the example of FIG. 1, the balloon catheter 101 is disposed in a delivery sheath 140. In other embodiments, the delivery sheath 140 is not included. In some embodiments that have a delivery sheath, the delivery sheath 140 is a hollow tube that can be initially placed inside a patient and subsequently used as a conduit for other medical devices, such as the balloon catheter 101. For procedures in which several catheters may be employed (e.g., catheters of different sizes or having different characteristics or functions), the delivery sheath 140 can protect the patient's internal body organs and body lumens through which the various medical devices are navigated. In addition, the delivery sheath 140 can facilitate easier navigation of other medical devices, by a physician or other technician, to a treatment site.

The delivery sheath 140 may be steerable, and it may be characterized by a specific diameter, length, distal feature, etc. For example, delivery sheaths may be available in varying diameters, such as 8.5 Fr (French), 10 Fr, 11 Fr, etc.;

varying lengths, such as 60 cm, 65 cm, 71 cm, 78 cm, 90 cm, etc.; and having distal ends that are biased in various shapes, such as, for example, in a 15° curve, a 55° curve, a short 120° curve, a long 120° curve, etc. Different delivery sheaths may be configured for different procedures. For example, a delivery sheath having one biased curvature may be particularly effective for guiding an inner balloon to a patient's pulmonary veins to treat atrial fibrillation, while a delivery sheath having a different biased curvature may be particularly effective for another procedure, such as one in which a stent is delivered and positioned within a patient's vasculature.

In some embodiments, as depicted in FIG. 1, a distal tip 145 of the delivery sheath 140 is slightly tapered, for example, to facilitate navigation of the tip 145 through a patient's vasculature, or to facilitate crossing of tissue membranes of the patient (e.g., the septal wall, during a procedure to treat atrial fibrillation). A proximal end 148 may be tapered to more easily receive other medical devices, such as the balloon catheter 101 that is shown disposed in the delivery sheath 140.

Exemplary cryotherapy catheters can include other components and structures that are not shown in FIG. 1. In particular, for example, a cryotherapy catheter may include one or more temperature sensors in chamber 119, on or in the balloon, on a shaft 110, etc. A pressure sensor, e.g., a pressure sensing lumen, can be included to detect pressure within inner balloon 104 or, as discussed above, in the space between the inner and outer balloons. Various electrodes can be included on the outer balloon 106 (e.g., to sense electrical activity in tissue to potentially be treated, or to stimulate electrical activity in such tissue). Other features are possible and contemplated.

Figure 3:
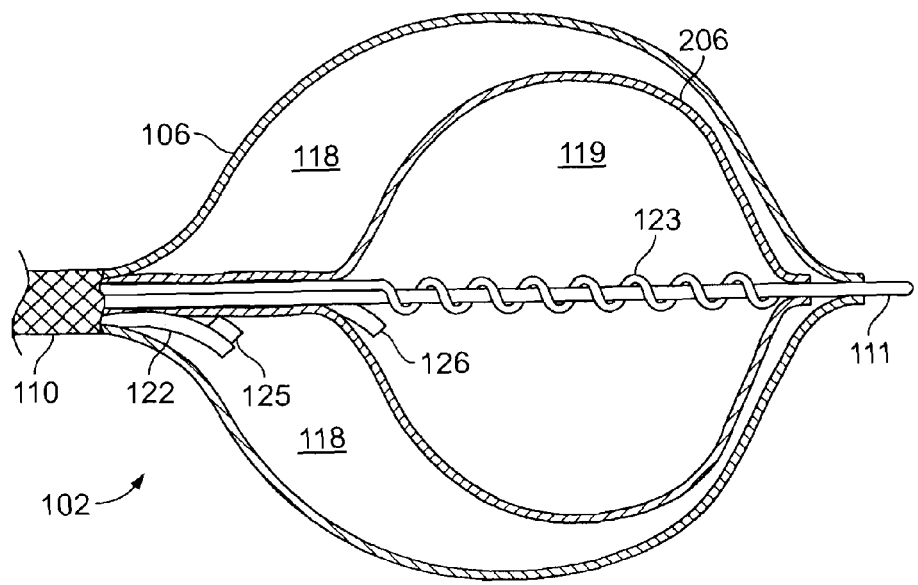
FIG. 3 illustrates another example implementation of double balloon cryotheraphy catheter.

By having a double balloon design where a small positive pressure is maintained between the outer balloon and the inner balloon, cyrotherapy can be limited to the tissues that pressed against the outer balloon 106 with sufficient strength to make the outer balloon 106 contact the inner balloon 104 in that region. For example, when the double balloon is pressed against the pulmonary vein wall, as shown in FIG. 2, the cryoablation region can be limited to that annular contact region 202 where the balloons contact each other and press against the pulmonary vein wall. The placement of the cryoablation contact region can be determined by the shapes and/or positioning of the inner balloon 104 and the outer balloon 106. For example, as shown in FIG. 3, the inner balloon can be positioned towards a distal end of the outer balloon such that the balloons preferentially contact each other at a distal end of the inflatable balloon portion. Arrangement and shapes of the two balloons can be adapted for particular applications of cryotherapy. In other embodiments, certain portions of the outer and inner balloons can be positioned to always be in contact. For example, certain portions of the inner and outer balloons can be adhered.

Figure 4A:
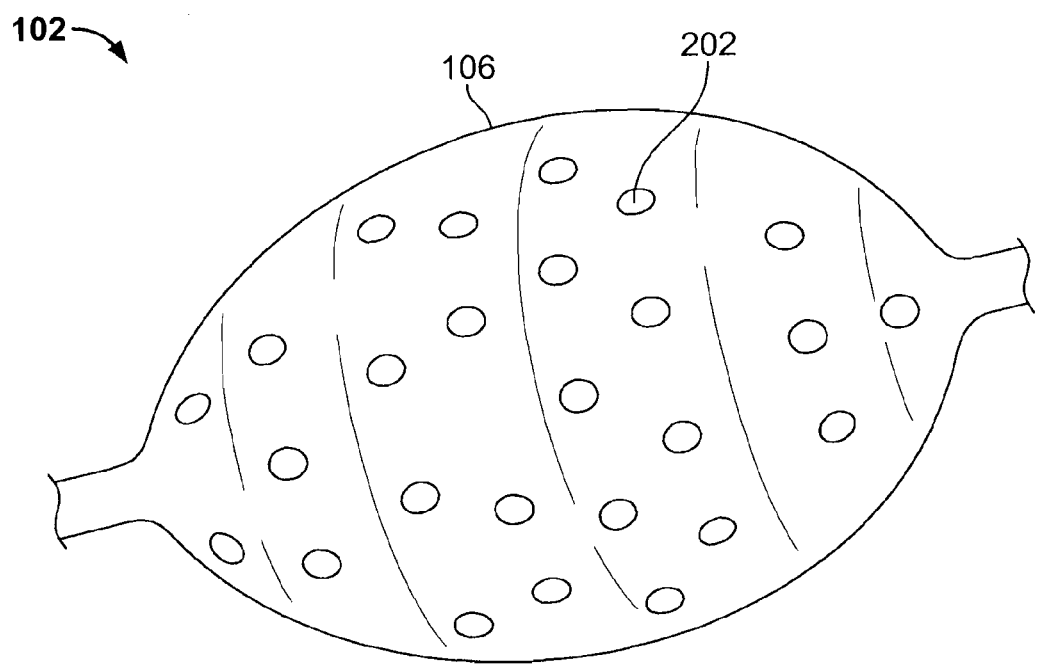
FIGS. 4A-4G illustrate example embodiments of a double balloon catheter having an outer balloon having a wall having compressible structures.

An outer balloon 106 can also be designed to include compressible structures. For example, outer balloons 106 having compressible structures are depicted in FIGS. 4A-4G. As shown in FIG. 4A, a series of compressible structures 202 can be uniformly arranged about the wall of the outer balloon 106. The compressible structures 202 can separater the inner balloon from an outer surface of the outer balloon and thus insulate body tissues and fluids from any cryotherapy agent within the inner balloon. When the cryotherapy catheter is manipulated to press the outer balloon against a target tissue region, however, the compressible structures in the region of the outer balloon wall adjacent the target tissue region can be compressed between the target tissue region and the inner balloon and thus allow for a better transfer of heat from the target tissue region to the inner balloon. Accordingly, cryotherapy can be applied to a target tissue region while insulating surrounding non-target tissues.

Figure 4B:
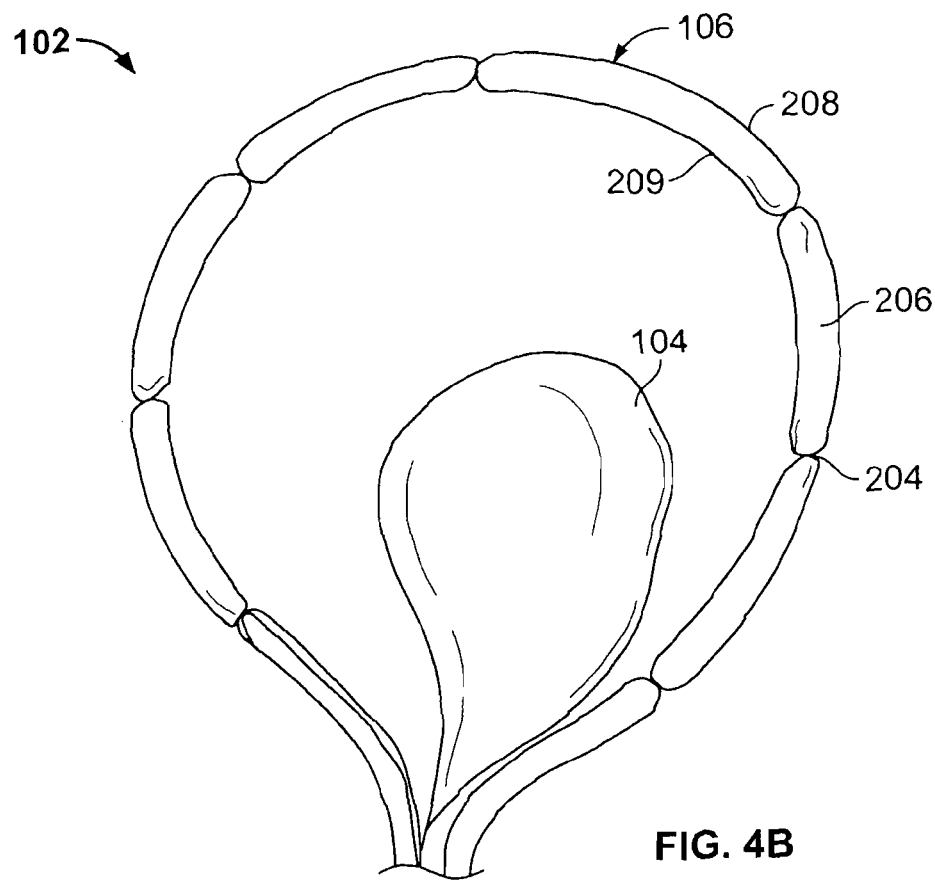
Figure 4C:
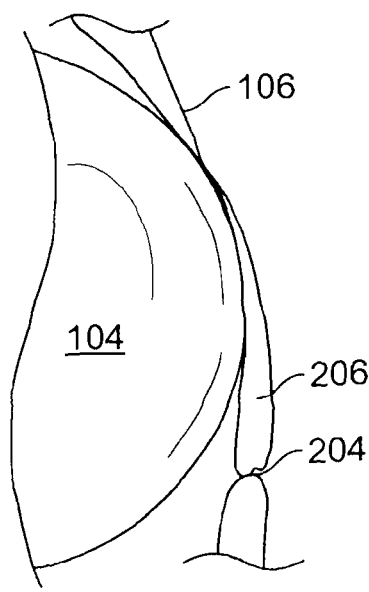

FIG. 4B depicts an implementation of the outer balloon 106 having an inner wall 209 and an outer wall 208 that define a fixed fluid filled pockets 206 therebetween. The pockets 206 can be filled with an insulating fluid, e.g., a gas or liquid such as those discussed above. In other embodiments, the pockets 206 can be filled with a gel. The inner wall 209 and the outer wall 208 are connected by ribs 204 that hold the walls together. The ribs 204 allow for fluid to pass from each pocket 206 to adjacent pockets 206. Accordingly, as shown in FIG. 4C, when the outer balloon 106 is pressed against a target tissue region, such an adjacent region of the outer balloon 106 is compressed between the target tissue region and the inner balloon 104, fluid in the pockets 206 in the compressed portion of the outer balloon 106 flows through ribs 204 to adjacent pockets and thus allows for better heat transfer between the target tissue region and the inner balloon. As shown in FIG. 4E, the outer balloon 106 can also include smaller compressible pockets 222. The compressible pockets 222 can also be filled with an insulating fluid. In other embodiments, as shown in FIG. 4G, the outer balloon can include an open cell foam that can be compressed under pressure to reduce its insulating effects.

Figure 4D:
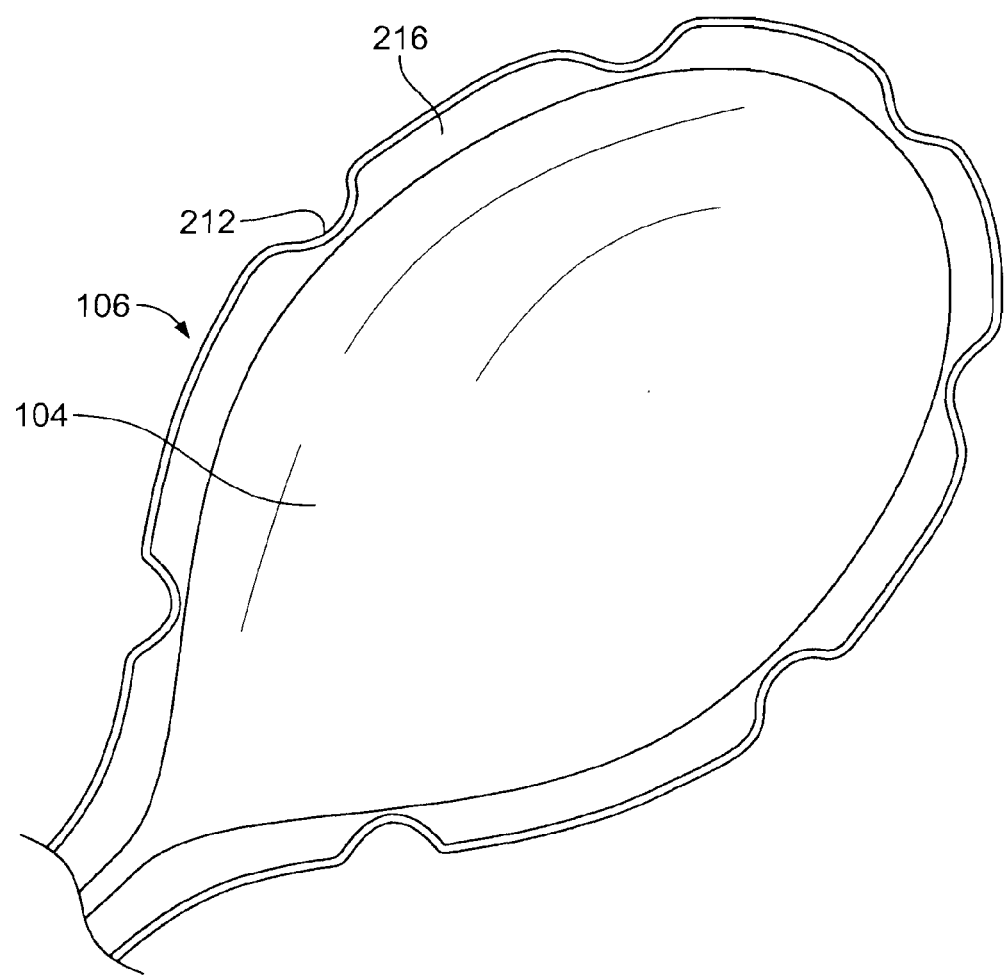
Figure 4E:
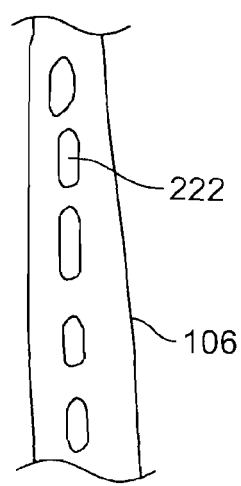

FIG. 4D depicts an implementation of an outer balloon 106 having preformed dimples 212. The preformed dimples 212 can be uniformly positioned about the outer balloon. The dimples 212 preferentially contact the inner balloon such that the majority of outer balloon is spaced from the inner balloon by fluid space 216. The fluid space insulates the majority of the outer balloon from the inner balloon. Accordingly, when the outer balloon 106 is pressed against a target tissue region, such an adjacent region of the outer balloon 106 is compressed between the target tissue region and the inner balloon 104, the preformed dimpled deform to allow the portion of the outer balloon 106 adjacent the target tissue region to contact the inner balloon 104 and thus allow for better heat transfer between the target tissue region and the inner balloon.

Figure 4F:
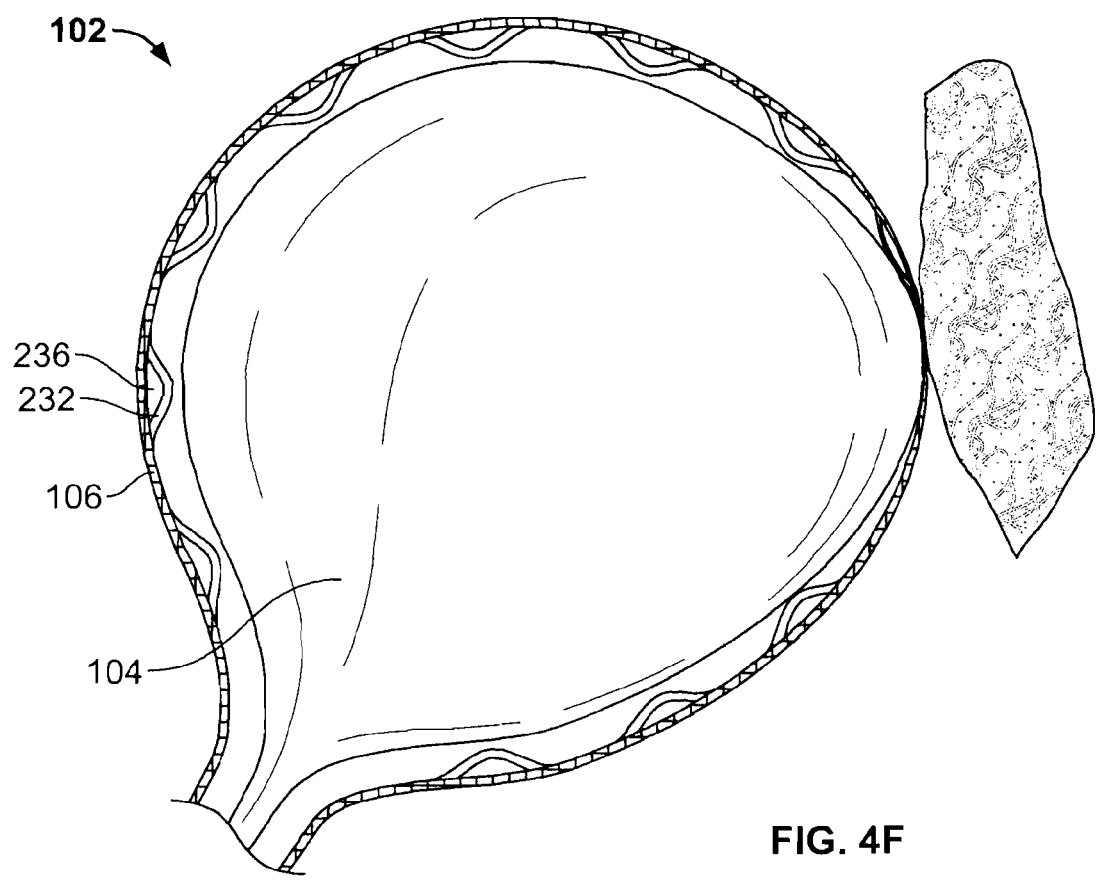
Figure 4G:
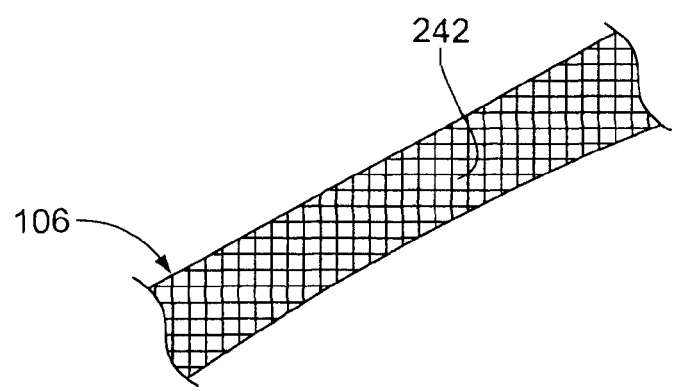

FIG. 4F depicts an implementation of an outer balloon 106 having internally formed collapsible bumps 232. The bumps 232 can define an internal space 236. Internal spaces 236 can include a fluid. For example, the internal spaces 236 can be filled with a gas or liquid such as those discussed above. In other embodiments, the internal spaces 236 can be filled with a gel. In some embodiments, the outer surface of the outer balloon is smooth. The collapsible bumps can position the inner balloon away from the outer balloon. The collapsible bumps are adapted to collapse when the outer balloon is compressed between a target tissue region and the inner balloon 104.

Figure 5:
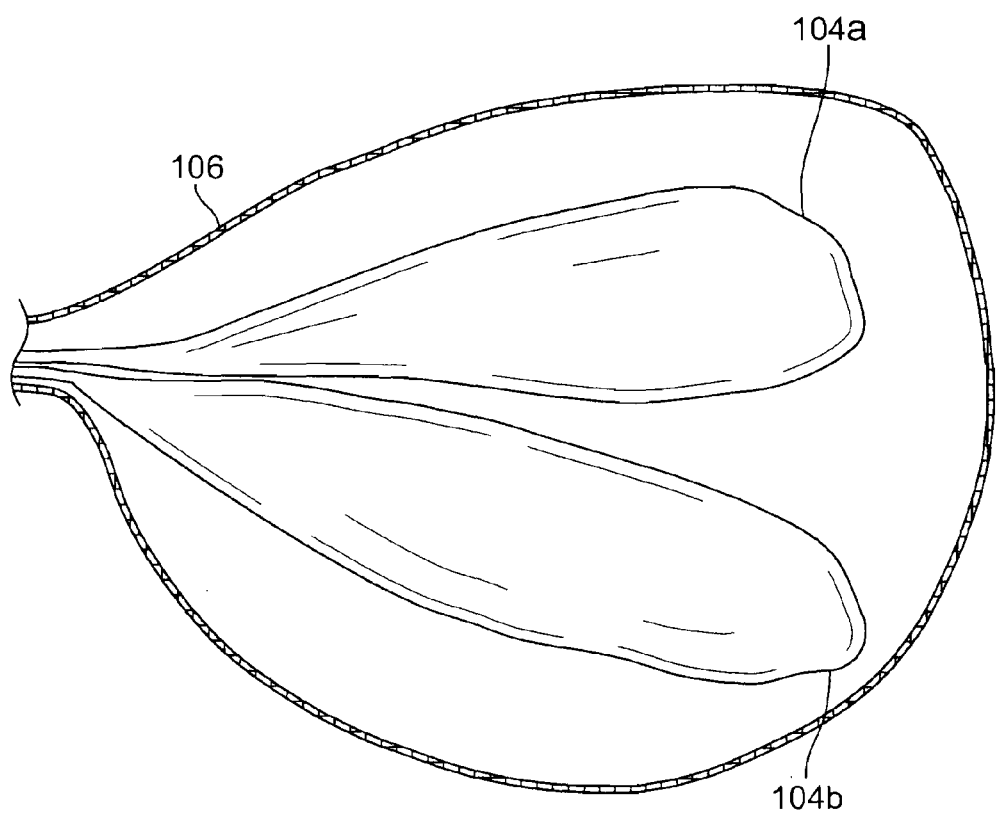
FIG. 5 illustrates an example implementation of a balloon catheter having multiple inner balloons within an outer balloon.

FIG. 5 depicts an implementation of an inflatable balloon portion having two inner balloons 104A and 104B nested within outer balloon 106. The two inner balloons can be alternatively inflated with a cryogenic agent and/or an insulating fluid to control the portions of the outer balloon 106 that contact portions of an inner balloon that includes a cryogenic agent. In other embodiments, the inflatable balloon portion 102 can include additional inner balloons and/or can include a subdivided inner balloon.

Figure 6:
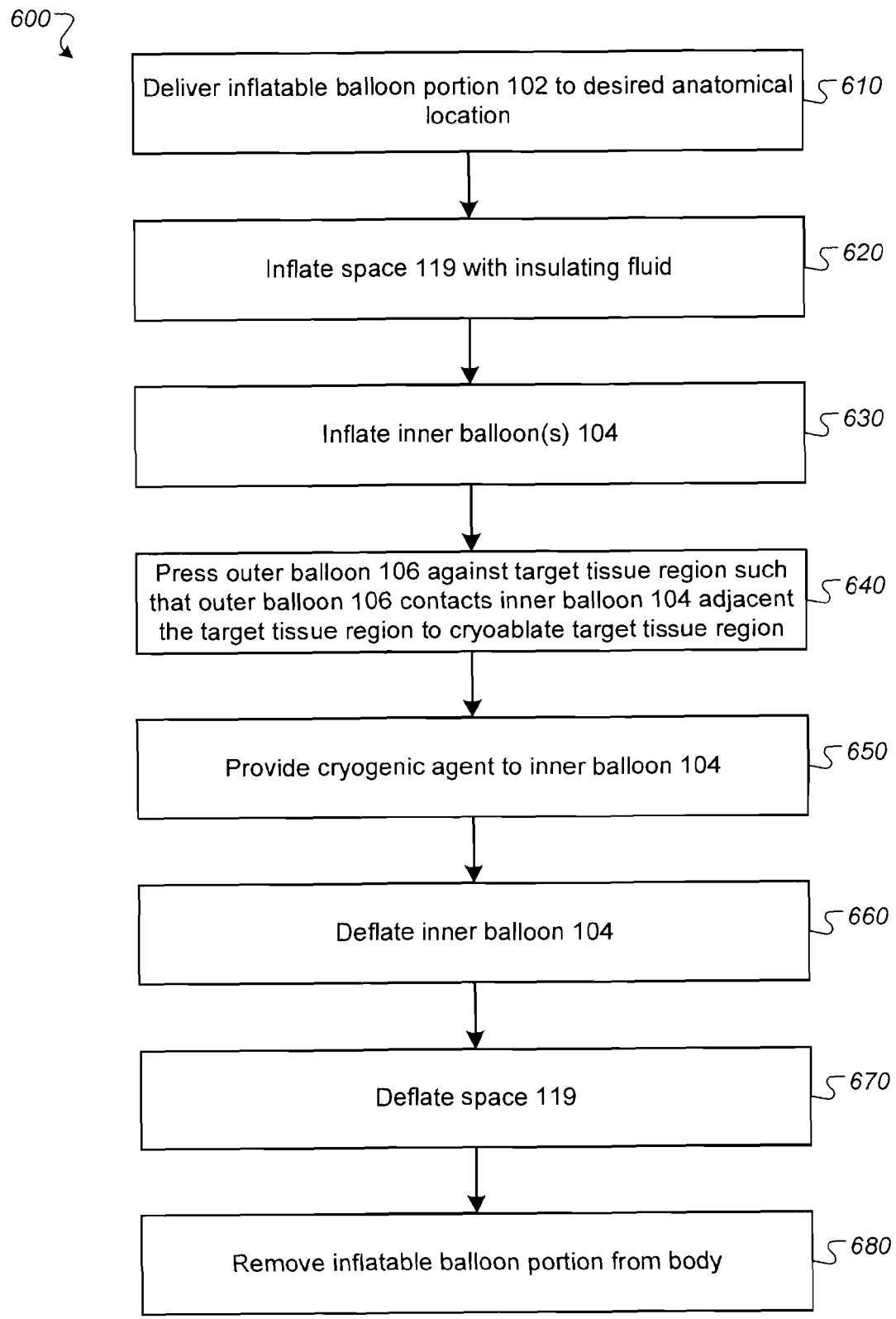
FIG. 6 is a flow chart with steps of using the cyrotherapy system of claim 1.

FIG. 6 is a flowchart of a process of using the cyrotherapy system of FIG. 1. The process 600, includes a first step of delivering a distal end of the cryotherapy catheter to a desired anatomical location 610. The desired anatomical location can be adjacent to a target tissue region for cyrotherapy. A distal end includes an inflatable balloon portion including an outer balloon 106 and an inner balloon 104 nested within the outer balloon. During the delivery process, the inner and outer balloons are deflated. The delivery process can include passing the distal end of the cryotherapy catheter though a sheath. In some embodiments, the cryotherapy catheter is delivered into or adjacent to the heart.

Once the distal end of the cryotherapy cather is delivered to a desired anatomical location, the process 600 includes a step of inflating the inflatable balloon portion 102. The space between the inner balloon and the outer balloon is inflated with an insulating fluid in step 620 to provide an insulating layer between the inner balloon and surrounding tissues and body fluids. The inner balloon is inflated in step 630. A pressure between the inner balloon 104 and the outer balloon 106 can be monitored via a presser sensor to detect pressure changes indicating a leak in either the inner and/or outer balloon. The pressure can be monitored throughout the procedure.

Once the inner and outer balloons are inflated, the inflatable balloon portion 102 is pressed against the target tissue region in step 640 in order to have the outer balloon 106 deform to contact a portion of the inner balloon 104 adjacent to the target tissue region. For example, as shown in FIG. 2, when pressed against a pulmonary vein wall, the cryoablation can be limited to a contact region 202 between the two balloons, as shown in FIG. 2. The inner balloon 104 then receives a cryogenic agent in step 650 to provide a means to extract heat form a target tissue region. In some embodiments, the treatment pattern shape corresponds to at least a portion of a Maze pattern. The inflatable balloon portion 102 can be configured to be inflated inside a patient's left atrium in a manner in which the external surface of the outer balloon 106 contacts multiple pulmonary vein ostia (e.g., the left superior pulmonary vein and left inferior pulmonary vein). The treatment pattern shape can be configured to ablate tissue around multiple corresponding ostia (e.g., in a pattern corresponding to at least a portion of the ablation patterns). For example, the cryotherapy catheter can be routed to the patient's left atrium through the patient's femoral vein, into the inferior vena cava and right atrium, through the septal wall, and into the left atrium. Cyrotherapy catheters can also be employed in various other procedures and/or be routed to a desired anatomical location via other paths.

Once the cryotherapy is completed, the inflatable balloon portion 102 is deflated to allow for the cryotherapy catheter to be removed from the anatomical location. The inner balloon 104 is deflated in step 660 to have the inner balloon retract without interference from the outer balloon 106. The space 119 between the inner balloon 104 and the outer balloon 106 is deflated in step 670 to fully deflate the inflatable balloon portion 102. By deflating the inner balloon first while maintaining the positive pressure in the space between the inner and outer balloons reduces that chances that the inner and outer balloons will interact causing the balloons to fold in improper ways that would complicate the extraction of the inflatable balloon portion 102. Once the inflatable balloon portion 102 is fully deflated, the distal end of the cryotherapy catheter is removed from the body in step 680.

The use of the outer balloon 106 insulates non-target tissues and surrounding body tissues from the cryogenic agents within the inner balloon 104. Accordingly, less heat is absorbed by the cryogenic agents within the inner balloon 104, thus reducing the amount of cryogenic agent needed to successfully complete the cyrotherapy of the target tissue region. Furthermore, the outer balloon 106 occupies a larger space internally than the inner balloon and can be complaint with body tissues. Accordingly, the outer balloon 106 can conform to the surrounding body tissues, including non-target tissue regions. For example, the outer balloon can also be used to reduce the flow of blood to the target tissue region. The outer balloon can, in some embodiments, be a compliant balloon and be inflated to variable diameters/shapes (depending on pressure) in order to obtain occlusion regardless of a variety of anatomical geometries, including non-symmetrical anatomical geometries.

A number of ancillary processes may be used to affect the material properties of the balloons 104 and/or 106. For example, the polymer extrusion may be exposed to gamma radiation which can alter the polymer infrastructure to provide uniform expansion during blow molding and additional burst strength when in use. In addition, the formed balloons 104 and/or 106 may be exposed to a low temperature plasma field which can alter the surface properties to provide enhanced adhesion characteristics. Other materials and manufacturing processes can be used to provide the balloons 104 and/or 106 with desired characteristics.

A number of embodiments have been described. Nevertheless, it will be understood that various modifications may be made without departing from the spirit and scope of this document. In particular, for example, cryotherapy balloon catheters are described as employing the Joule-Thomson effect to cool using a liquid-to-gas phase change, but liquid-based cryocatheters can also include cooling regions and thermally insulated regions. Moreover, cryotherapy catheters can be employed to deliver targeted cryotherapy to regions of a patient's body other than the patient's heart (including, for example, a patient's prostate gland, or other glands; a portion of the patient's gastro-intestinal tract; a small (e.g., varicose) vein; or other suitable internal treatment sites). Multiple cooling and thermally insulating regions can be provided, and the regions can be formed in various shapes and sizes. Accordingly, other embodiments are within the scope of the following claims.

What is claimed is:
1. A cryotherapy system comprising:
 a cryotherapy catheter comprising an inflatable balloon portion at a distal end of the cryotherapy catheter, the inflatable balloon portion having an outer balloon and an inner balloon within the outer balloon, the inner balloon configured to receive during a cryotherapy procedure a cryogenic agent for extracting heat from body tissue at a desired location, wherein the outer balloon includes a plurality of deformable structures configured to contact the inner balloon such that a majority of the outer balloon is spaced from the inner balloon, wherein deformation of the plurality of deformable structures allows a portion of the outer balloon adjacent to the plurality of deformable structures to contact the inner balloon; and
 a pressure regulator to maintain a positive pressure between the inner balloon and the outer balloon during a cryotherapy procedure.
2. The cryotherapy system claim 1, further comprising a detector to monitor the pressure between the inner balloon and the outer balloon and to determine whether a leak of the inner or outer balloon has occurred.
3. The cryotherapy system of claim 1, wherein the pressure regulator is configured to maintain a positive pressure between the inner balloon and the outer balloon sufficient to maintain a fluid space between the inner balloon and the outer balloon when the outer balloon is within a body lumen.

4. The cryotherapy system of claim 1, wherein the pressure regulator is configured to maintain a positive pressure of between 0.1 and 2 psi greater than blood pressure.

5. The cryotherapy system of claim 1, wherein the pressure regulator comprises a valve and is configured to maintain the positive pressure by closing the valve once a space between the outer balloon and the inner balloon is filled with a predetermined amount of fluid.

6. The cryotherapy system of claim 1, wherein the outer balloon is more compliant than the inner balloon.

7. The cryotherapy system of claim 1, wherein the outer balloon comprises a material selected from the group consisting of urethane, polyether block amide, and combinations thereof.

8. The cryotherapy system of claim 1, wherein the plurality of deformable structures are deformable dimples.

9. The cryotherapy system of claim 1, wherein the plurality of deformable structures are collapsible bumps.

10. The cryotherapy system of claim 9, wherein an outer surface of the outer balloon is smooth.

11. The cryotherapy system of claim 9, wherein the collapsible bumps define a plurality of internal spaces.

12. The cryotherapy system of claim 11, wherein the internal spaces include at least one of a gas and a liquid.

13. A cryotherapy catheter comprising:
    an inflatable balloon portion at a distal end of the cryotherapy catheter, the inflatable balloon portion including:
        an inner balloon adapted to receive a cryotherapy agent; and
        an outer balloon including a plurality of deformable structures configured to contact the inner balloon such that a majority of the outer balloon is spaced from the inner balloon, the inner balloon being within the outer balloon such that the plurality of deformable structures are adapted to be deformed between a target tissue region and the inner balloon to allow a portion of the outer balloon adjacent to the target tissue region to contact the inner balloon and provide for better heat transfer between the between the target tissue region and the inner balloon.

14. The cryotherapy catheter of claim 13, wherein the outer balloon is more compliant than the inner balloon.

15. The cryotherapy catheter of claim 13, wherein the outer balloon comprises a material selected from the group consisting of urethane, polyether block amide, and combinations thereof.

16. The cryotherapy catheter of claim 13, wherein the plurality of deformable structures are deformable dimples.

17. The cryotherapy catheter of claim 13, wherein the plurality of deformable structures are collapsible bumps.

18. The cryotherapy catheter of claim 17, wherein the collapsible bumps define a plurality of internal spaces.

19. The cryotherapy catheter of claim 18, wherein the internal spaces contain a fluid.

20. The cryotherapy catheter of claim 18, wherein the internal spaces contain a gel.

* * * * *